United States Patent [19]

Dyer et al.

[11] Patent Number: 4,925,669

[45] Date of Patent: May 15, 1990

[54] THERAPEUTIC COMPOSITIONS FOR VETERINARY USE

[76] Inventors: Alan Dyer, 4 Park Road, Manchester M8 6HU; Phyllis D. Wells, 4 Monks Hall Grove, Eccles M30 9GL; Craig D. Williams, 1 Whitburn Drive, Brandlesholme, Bury, Lancashire BL8 1EH, all of United Kingdom

[21] Appl. No.: 124,788

[22] PCT Filed: Mar. 3, 1987

[86] PCT No.: PCT/GB87/00147

§ 371 Date: Nov. 16, 1987

§ 102(e) Date: Nov. 16, 1987

[87] PCT Pub. No.: WO87/05504

PCT Pub. Date: Sep. 24, 1987

[30] Foreign Application Priority Data

Mar. 15, 1986 [GB] United Kingdom ............... 8606468

[51] Int. Cl.$^5$ .............................................. A23K 1/18
[52] U.S. Cl. .................................... 424/438; 424/439; 424/440; 424/441

[58] Field of Search ............... 424/440, 438, 439, 441

[56] References Cited

U.S. PATENT DOCUMENTS

| 2,439,532 | 4/1948 | Whiting et al. | 424/442 X |
| 2,918,403 | 12/1959 | Brooks et al. | 424/438 |
| 3,514,204 | 11/1970 | Sibbald et al. | 424/438 |
| 3,617,299 | 11/1971 | Mattdon et al. | 424/442 X |
| 3,891,759 | 6/1975 | Aries | 424/416 X |
| 4,046,753 | 9/1977 | Fisher et al. | 424/442 X |
| 4,352,891 | 10/1982 | Quinlan | 424/79 X |
| 4,564,363 | 1/1986 | Bagnall et al. | 424/438 |

FOREIGN PATENT DOCUMENTS 2094624 9/1982 United Kingdom ............... 424/442

Primary Examiner—Thurman K. Page
Attorney, Agent, or Firm—Young & Thompson

[57] ABSTRACT

A therapeutic composition for veterinary use comprises a therapeutic agent associated by sorption and/or adsorption with a substrate selected from zeolites and pillared clays.

6 Claims, 2 Drawing Sheets

RELEASE PROFILE FOR DDVP FROM NAY (DRIED) TO WATER AT 80° C

THERAPEUTIC COMPOSITIONS FOR VETERINARY USE

This invention relates to compositions having therapeutic properties, which are particularly useful in veterinary practice.

It is common practice to administer drugs and other therapeutic agents to animals, either to treat infections and other undesirable conditions or to produce and/or maintain good health and other desirable conditions. It has now been discovered that a wide range of compositions for such purposes can be made, by a number of methods which also form aspects of this invention. The compositions of the invention contain the desired therapeutic agent, or agents in association with carrier or substrate substances as explained below. It has also been discovered that known beneficial effects of the carrier substances can be produced in conjunction with the desired effects of the therapeutic agents. Furthermore, the preferred carrier substances have been found to act as slow-release agents and so give improved performance by the therapeutic agent involved.

In accordance with an aspect of this invention, a therapeutic composition comprising at least one veterinary therapeutic agent is characterised in that the composition includes at least one substrate selected from zeolites and pillared clays, with which the therapeutic agent is associated by internal sorption and/or external adsorption. For simplicity, the term "drug" is used below to describe any therapeutic agent suitable for use in accordance with this invention. A preferred feature of the invention is the use, as the therapeutic agent, of at least one anthelmintic agent.

In accordance with another aspect of this invention, a method of manufacture of a therapeutic composition comprising at least one veterinary therapeutic agent is characterised in that the therapeutic agent in solution or vapour form is brought into contact with a substrate selected from zeolites and pillared clays comprising at least one zeolite compound and/or pillared clay, for a time sufficient to allow a significant amount of the agent to become associated by internal sorption and/or external adsorption with the substrate and, if required, the resultant composition is caused or allowed to dry. In appropriate instances, a solution can be contacted with the zeolite compound or other substrate which contains 2 or more drugs which are desired in the resultant composition. Alternatively, a composition containing two or more drugs can be made by contacting the zeolite and/or pillared clay substrate in sequence with a solution of each of the drugs of interest.

Zeolites are hydrated alumino-silicates, having framework structures enclosing cavities and channels, which can contain mobile cations and water molecules. As is known, zeolites can undergo reversible ion exchange and water loss reactions and they also have molecular sieve properties. The general formula of zeolites, both as natural and synthetic forms, is as follows:

$(M^I_2, M^{II}O)(Al_2O_3 \cdot n\ SiO_2)\ m\ H_2O$.

where $M^I$ and $M^{II}$ are monovalent and divalent cations respectively, n can have any value from 1 upwards and m can have any integral or fractional value in the range from 0 to 5. Modern synthetic techniques allow either or both of the Al and Si atoms to be replaced by atoms of other elements in the zeolite framework. Replacement can also be effected by altering existing zeolite substances. Elements introduced in this way include P, for Si, as in AlPO compounds and many others, such as Be, Zn, Sn, Fe, B, Ga, Ge, Zr and Ti. Another variant involves the substitution of $M^{III}$, i.e. trivalent ions, for at least part of the $M^I$ and $M^{II}$ in the general formula. $M^I$, $N^{II}$ and $M^{III}$ can be selected from any desired inorganic and organic cations. Thus the chemical modification of zeolites has previously been concerned with ion replacement or the physio-chemical attachment of ions or small molecules, such as water.

Clays which have been treated in known manner so that the individual platelets or other particles are more widely spaced, namely pillared clays, are also useful as substrates for the veterinary compositions of the invention.

It has now surprisingly been discovered that certain drug molecules can be associated with zeolites and pillared clays and can be delivered to animal hosts, when the resultant compositions are administered. The mechanism involved in forming these compositions can be internal, external or both, for instance by sorption inside the zeolite or clay cavities, by adsorption upon the zeolite crystal or clan particle surfaces or by both internal sorption and external adsorption in the same composition. It is surprising to find that even relatively large drug molecules can be easily and specifically taken up by these substrates, such as zeolites, from both aqueous and polar solvents. Even more surprising is the discovery that such drug molecules can then be released, when the resultant complexes or compositions are subsequently administered, e.g. to animals in carrying out a worming or other veterinary treatment. From the previous knowledge of the behaviour of zeolites, for instance, it was not to be expected that such complexes would lead to a release of the drug component. Moreover, a further aspect of the surprising behaviour in use of compositions according to the invention is that release of the one or more drugs associated with the zeolite or pillared clay component in a coat position according to the invention takes place slowly and in a largely even and regular manner, so that release takes place in a most advantageous manner. As will appear from the following part of this description, it has been established that release of the drug component is not only steady and very even, but is initiated almost immediately when administration has occurred.

The drug or drugs present in the therapeutic composition do not lose their properties and can be administered in any suitable way, for instance by mixing a composition according to the invention, in powder form, with animal feedstuffs or by forming the composition into pellets and administering these as such or by addition to feedstuffs. It has been suggested already that zeolites are themselves beneficial, when given to animals, for instance pigs, poultry, cattle, sheep and goats, for instance in a ratio of 5% to 10% by weight of feedstuffs. Thus the therapeutic compositions of the invention can be used effectively to produce, by way of example, the known beneficial effects of zeolites and the desired and known beneficial effects of the therapeutic agents present in the compositions of the invention and that these effects are manifested at the same time and without either component affecting the beneficial actions of the other. It has also been discovered that the compositions of the invention, when administered, allow the relatively slow and controlled release of the drugs into the gastric and circulatory systems of the animal.

Figure 1:
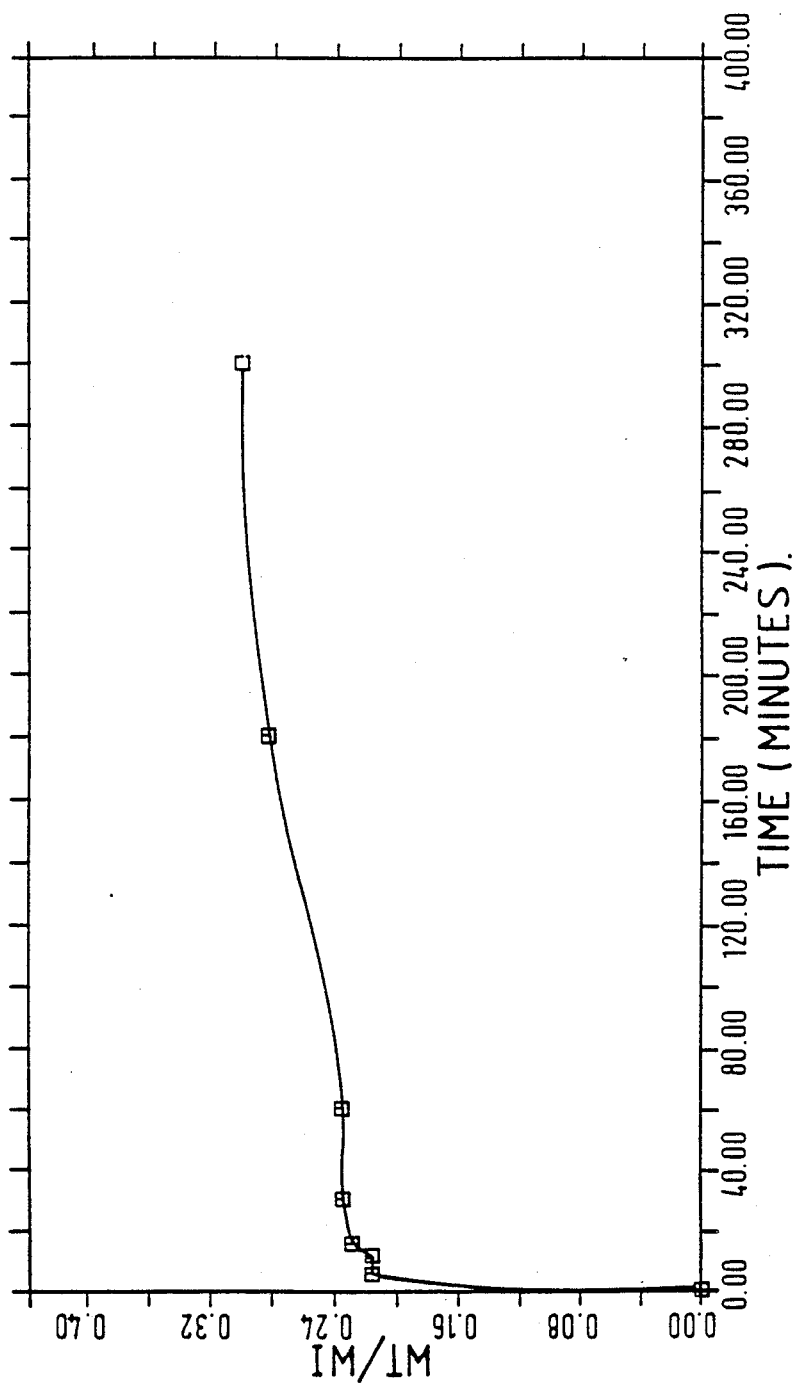
FIGS. 1 and 2 describes the various release profiles for DDVP.

In order to illustrate the invention and allow it to be fully appreciated and understood, various preferred techniques are described below, together with examples of the manufacture of therapeutic compositions according to the invention and test results given when they are used. These techniques and examples are described in connection with zeolite substrates, for convenience, and it is to be understood that the same applies to the use of pillared clay substrates or to the use of both kinds of substrate materials in conjunction.

According to one preferred embodiment of the method of the invention, contact between the agent and the zeolite component involves use of a solution of the agent; this can either be passed through a column of the zeolite component in powder or pellet form or can be slurried with a quantity of it in powder, aggregate or pellet form. In another preferred embodiment, an agent capable of vaporisation is contacted in vapour form with the zeolite component while contained in an enclosure.

In the following part of the description, X and Y designate synthetic faujasite, used in the Na, Ba and Cs forms, Z 900 indicates a synthetic mordenite, in its Na form while NaA indicates the sodium form of zeolite A. Therapeutic compositions according to the invention have been made with all of these zeolites and all of the following anthelmintic drugs:

Dichlorovos (DDVP)
Fenbendazole (FEN)
Levamisole (LEVA)
Tetramisole (TETRA)

Manufacture of therapeutic compositions using the zeolites and drugs mentioned above, has mainly been based upon contacting solutions containing the drug with the zeolite in powder or pellet form or by stirring the zeolite, in powder, aggregate or pellet form, into such a solution to form a slurry. Zeolites can be aggregated, in order to form suitable sized pellets, or they can be pelletized by mixing them with a clay-based mineral. Commercially, zeolites are obtainable in powder, aggregate ("self-bound") or pellet form. Solutions of the drugs have been used, in concentrations in the preferred range from 0.1 to 10% by weight, using water, carbon tetrachloride, methanol, dimethylformamide, tetrahydrofuran or mixtures thereof, as indicated in the following Table. It has been found preferable to use a solution of DDVP in water and $CCl_4$ in the range from 0.1 to 10%, a solution of FEN in dimethylformamide and tetrahydrofuran in the range from 0.1 to 1% and a solution of LEVA or TETRA in methanol in the range from 0.1 to 1%. After preparation of the compositions, all the solvents are recoverable by normal methods.

A loading solution of the drug, in the concentration indicated in the Table below, in a suitable solvent, is placed with a predetermined weight of the selected zeolite in a glass vessel and the vessel contents are stirred for 72 hours, using a PTFE stirrer. The zeolite is then filtered off and air-dried for four hours. The zeolite composition is then dried for 24 hours at 60° C. in a vacuum oven.

Methods of preparation of the compositions have also been used, which are essentially the same as above, but with increased temperature of the use of reflux conditions in the temperature range stated.

A further technique involves filling a glass or other column with, e.g., 1 to 5 grams of the zeolite in the form of powder, pellets or aggregate and allowing a solution containing a predetermined concentration of the selected drug to percolate through the column.

A fourth technique involves exposing a predetermined quantity of the selected zeolite in an enclosure and subjecting it to contact with the drug in vapour form.

Uptake of the drug on and/or into the zeolite carrier can be monitored by measuring the disappearance of the drug from the loading solution, using gas-liquid chromatography, UV spectrometry or radio-labelling, to determine the concentration of the drug left in solution. Thermal analysis (DTA, DSC or TG) can be used to determine drug loading levels on the zeolite carrier.

TABLE

| Zeolite | Solvent | Drug | Zeolite wt. g | Vol of loading solution | % Drug in solution | Loading of zeolite. mg drug per g zeolite |
|---|---|---|---|---|---|---|
| NaY | $H_2O$ | DDVP | 5 | 500 | 0.9 | 5 |
| NaY | $CCl_4$ | DDVP | 5 | 500 | 10.0 | 115 |
| NaY | $CCl_4$ | DDVP | 5 | 500 | 1.0 | 215 |
| NaY | Vapour phase | DDVP | 5 | 20 | vapour | 269 |
| NaY | $CCl_4$ | DDVP | 5 | 500 | 1.0 | 80 |
| NaY | $CCl_4$ | DDVP | 5 | 500 | 4.0 | 75 |
| NaY | $CCl_4$ | DDVP | 5 | 500 | 2.0 | 75 |
| NaY | $CCl_4$ | DDVP | 5 | 500 | 0.9 | 60 |
| NaY | $CCl_4$ | DDVP | 5 | 500 | 0.5 | 55 |
| NaY | $CCl_4$ | DDVP | 5 | 500 | 0.1 | 12.5 |
| NaY | $CCl_4$ | DDVP | 5 | 502 | 0.05 | 7.5 |
| Na Mordenite | vap | DDVP | 5 | 20 | vapour | 90 |
| Z900 | $H_2O$ | DDVP | 15 | 30 | 10 | 33 |
| NaX(Pellets) | $CCl_4$ | DDVP | 0.1 | 10 | 1.0 | ~20 |
| NaA(Pellets) | $H_2O$ | DDVP | 0.1 | 10 | 1.0 | ~15 |
| NaY | MeOH | Tetra | 5 | 500 | 1.0 | 33 |
| NaY | DMF | Fen | 5 | 500 | 1.0 | 10 |
| NaY | THF | Fen | 1 | 100 | 0.5 | 10 |
| NaY | MeOH | Leva | 5 | 500 | 0.1 | 10 |
| NaY | MeOH | Leva | 5 | 100 | 1.0 | 30 |

In order to evaluate the rate of release of the drug from a therapeutic composition according to the invention, these were contacted with artificial gastric juice at room temperature. The amount of the drug released into solution was measured as a function of time. Analyses were carried out by radio labelling, gas-liquid chromatography and chemical methods. The accompanying drawings show examples of the release profiles obtained in graphical form.

Animal Trials on Rat (6 rats per group).

Drug—tetramisole

Rats infected with 500 larva, Fed as follows:

Group A—Control fed no drug and no zeolite.
Group B—zeolite only at level in subsequent groups.
Group C—tetramisole at 15 mg/kg body weight (no zeolite).
Group D—zeolite loaded with drug dosed at 15 mg/kg body weight.
Group E—zeolite loaded with drug at 7.5 mg/kg body weight.

RESULTS

| GROUP | RESULTS LARVA DETECTED |
|---|---|
| A | 269 ± 27.4 |
| B | 274 ± 20.1 |
| C | 62 ± 18 |
| D | 5.2 ± 3.6 |
| E | 26.8 ± 10.3 |

| Group Pairing | Student Test P |
|---|---|
| A:B | No significant difference |
| A:C | <0.001 |
| A:D | <0.001 |
| A:E | <0.001 |
| C:D | p = 0.01 |
| C:E | No significant difference |
| D:E | No significant difference |

D has significantly less worms than C so zeolite +drug is more effective than drug alone.

Figure 2:
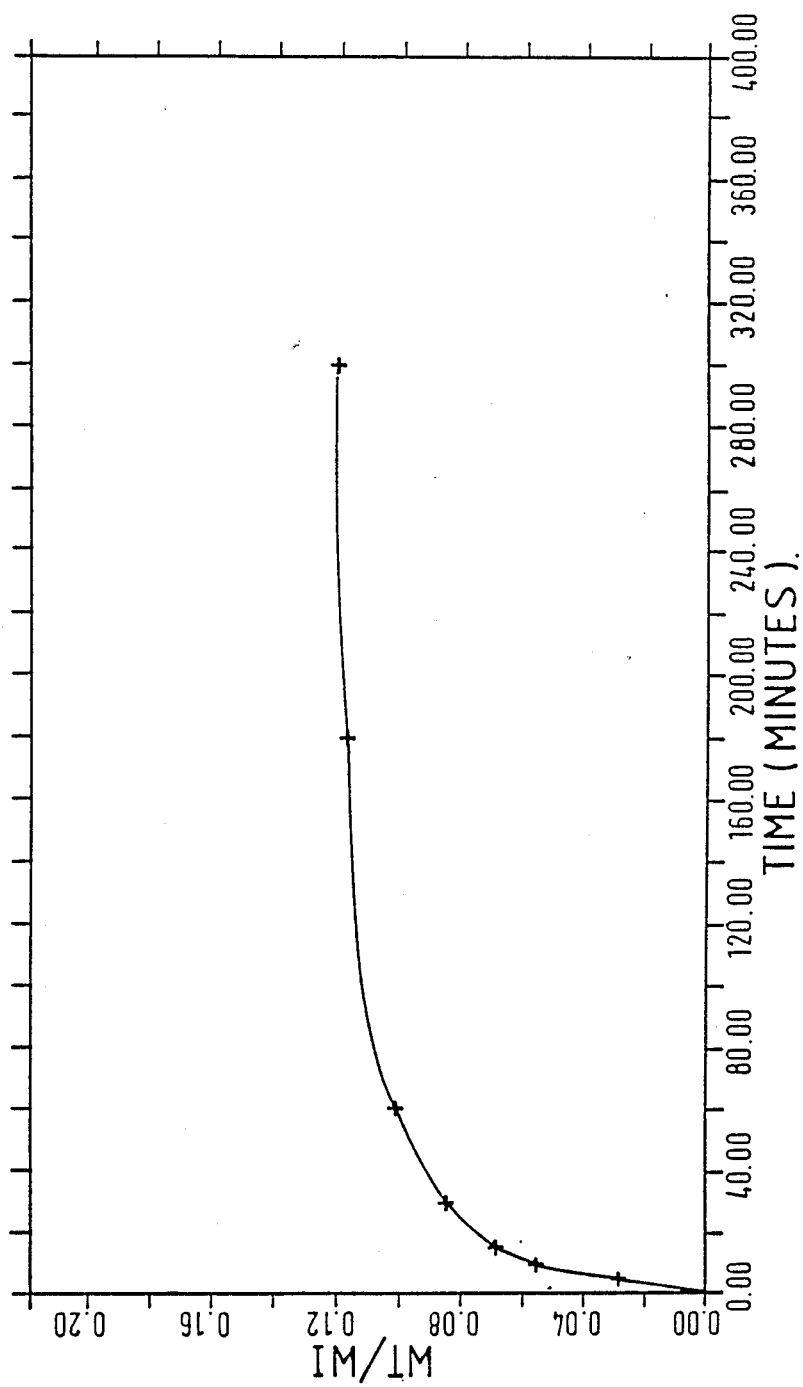

In order to demonstrate the behaviour of typical complexes according to the invention upon administration, reference is made to the accompanying drawings; each shows graphically a release profile, obtained by plotting wt/wi against time in minutes; FIG. 2 shows the release, profile for DDVP from Z900 at room temperature and FIG. 1 shows the release profile for DDVP from NaY at 80° C. It will be noted, in FIG. 2, that the rate of release rapidly increases over the first 60 minutes, reaching a value of 0.10 wt/wi at that time and then attaining a steady rate of about 0.12 wt/wi after another 30 minutes and maintaining this steady rate of, release for the remaining 210 minutes of the test. FIG. 1 shows an almost instantaneous attainment of a rate of over 0.20 wt/wi, followed by a period of much slower rate increase, until the rate generally levels out at about 0.28 wt/wi after around 160 minutes and maintaining this rate for the remainder of the test. Neither example shows any reduction in the rate of release.

We claim:

1. A therapeutic composition comprising at least one veterinary therapeutic agent, characterised in that the composition comprises at least one substrate selected from zeolites and pillared clays with which the therapeutic agent is associated by internal sorption and/or external adsorption.

2. A therapeutic composition comprising at least one veterinary therapeutic agent, characterised in that the composition includes a substrate comprising at least one zeolite, with which the therapeutic agent is associated by internal sorption and/or external adsorption.

3. A composition according to claim 1 or 2, wherein the substrate comprises at least one zeolite compound of the general formula:

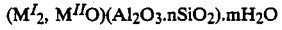

$$(M^I_2, M^{II}O)(Al_2O_3 . nSiO_2) . mH_2O$$

wherein $M^I$ and $M^{II}$ respectively represent monovalent and divalent cations or together represent at least in part a trivalent cation $M^{III}$, $M^I$, $M^{II}$ and $M^{III}$ each being selected from inorganic and organic cations, n has a value from 1 upwards and m has an integral or fractional value in the range from 0 to 5 and wherein either or both of the Al and Si atoms may be at least partly replaced within the zeolite framework structure with atoms of another element.

4. A composition according to claim 1, wherein the substrate is a zeolite component in powder, aggregate or pellet form and is selected from synthetic faujasite in any of the Na, Ba and Cs forms, synthetic mordenite in the Na form or the Na form of zeolite A and the therapeutic agent is an anthelmintic drug selected from Dichlorovos, Fenbendazole, Levamisole and Tetramisole.

5. A composition according to claim 1, wherein the therapeutic agent comprises at least one anthelmintic agent.

6. A composition according to claim 1, wherein the therapeutic agent is present in an amount in the range from 5 to 30 mg per gram of substrate.

* * * * *